(12) United States Patent
Kumar et al.

(10) Patent No.: US 8,278,913 B2
(45) Date of Patent: Oct. 2, 2012

(54) APPARATUS AND METHOD FOR POSITION SENSING

(75) Inventors: Dinesh Kumar, Grass Valley, CA (US); Guangyao Xu, Grass Valley, CA (US); Jasjit S. Suri, Roseville, CA (US)

(73) Assignee: Eigen Inc., Grass Valley, CA (US)

( * ) Notice: Subject to any disclaimer, the term of this patent is extended or adjusted under 35 U.S.C. 154(b) by 508 days.

(21) Appl. No.: 12/466,887

(22) Filed: May 15, 2009

(65) Prior Publication Data

US 2010/0004530 A1   Jan. 7, 2010

Related U.S. Application Data

(60) Provisional application No. 61/053,263, filed on May 15, 2008.

(51) Int. Cl.
*G01R 7/14* (2006.01)
*G01R 7/30* (2006.01)

(52) U.S. Cl. .................................................. 324/207.23

(58) Field of Classification Search .................. None
See application file for complete search history.

(56) References Cited

U.S. PATENT DOCUMENTS

| 7,777,481 B2* | 8/2010 | Singh et al. ............... 324/207.15 |
| 2008/0048653 A1* | 2/2008 | Sanders .................... 324/207.25 |

* cited by examiner

*Primary Examiner* — Paresh Patel
(74) *Attorney, Agent, or Firm* — Marsh Fischmann & Breyfogle LLP

(57) ABSTRACT

An improved apparatus and method for position sensing of a medical tracker device are presented. The apparatus and method are designed to constrain, rotate, and track the position of a medical tool. To improve the position sensing of the tracker, a joint that provides two degrees of freedom may use a revolute gear pair together with a rotary sensor for angular motion sensing and a sliding/prismatic assembly together with a linear magnetic sensor for linear position sensing. Thus, the linear motion sensing and the angular motion sensing are decoupled.

4 Claims, 9 Drawing Sheets

APPARATUS AND METHOD FOR POSITION SENSING

CROSS REFERENCE TO RELATED APPLICATION

This application claims the benefit of the filing date of U.S. Provisional Application No. 61/053,263, entitled: "Apparatus and Method For Position Sensing" having a filing date of May 15, 2008, the entire contents of which are incorporated herein by reference.

BACKGROUND

Apparatus for guiding medical tools have been shown to be of valuable assistance in various medical procedures, for example, manipulation of surgical tools, manipulation of cameras or sensors, biopsy, etc. An apparatus for guiding a medical tool usually also improves reproducibility compared to freehand medical procedures, for example, surgical or biopsy procedures.

These apparatus typically have one or more degrees of freedom and may be manually driven through these degrees of freedom with motive force being provided by a human practitioner, or may be automated in that at least one degree of freedom is driven by a computer controlled actuator. A medical tool often needs to be oriented about a point in, on, or in proximity to a patient's body. These apparatus can also monitor the position of the medical tool in a frame of reference such that the position of the tool can be identified in, for example, a medical image associated with the frame of reference. These apparatus are sometimes referred to as trackers.

Generally, trackers include one or more linkages that move relative to one another to position a medical tool relative to the patient. Most of the linkages are constrained to a single degree of freedom and thereby allow for precision measurement of their relative movement. Calculations (e.g. geometric calculations) use the relative movement between the linkages along with the lengths of the linkages to calculate the position of a free end of the tracker (end of the last linkage) in three-dimensional space. The last linkage typically supports the medical tool and often allows movement of at least two degrees of freedom. That is, the last linkage often allows for rotational movement and axial advancement or retraction of a medical tool. In the case of a TRUS ultrasound probe, this allows the probe to be advanced/retracted relative to a patient and rotated to acquire images. Therefore, the movement of the last linkage must be tracked in two dimensions. The provision of two degrees of freedom in this linkage complicates position sensing for this linkage and hence position sensing for the medical tool.

SUMMARY

An improved apparatus and method for sensing are presented. The apparatus and method are designed to constrain, rotate, and track the position of a medical tool. The apparatus is generally referred to as a tracker. In one arrangement, the medical tool is an end-fire trans-rectal ultrasound (TRUS) probe and/or a biopsy needle. The apparatus allows tracking such elements in three dimensional space to allow their reconstruction in a correct frame of reference in a 3-D ultrasound image acquired by, for example, the ultrasound probe. The apparatus and method can also be useful for other insertion trajectory into a small target area.

To improve the position sensing of the tracker, a joint that provides two degrees of freedom may use a revolute gear pair together with a rotary sensor for angular motion sensing and a sliding/prismatic assembly together with a linear magnetic sensor for linear position sensing. Thus, the linear motion sensing and the angular motion sensing are decoupled. The use of coupled revolute gears for angular sensing and a linear magnetic sensor avoids slippage seen in prior art trackers. Most of all, low maintenance, increased reliability, and much better accuracy in sensing, up to 1 μm, can be achieved using such a tracker design.

DETAILED DESCRIPTION

Figure 1:
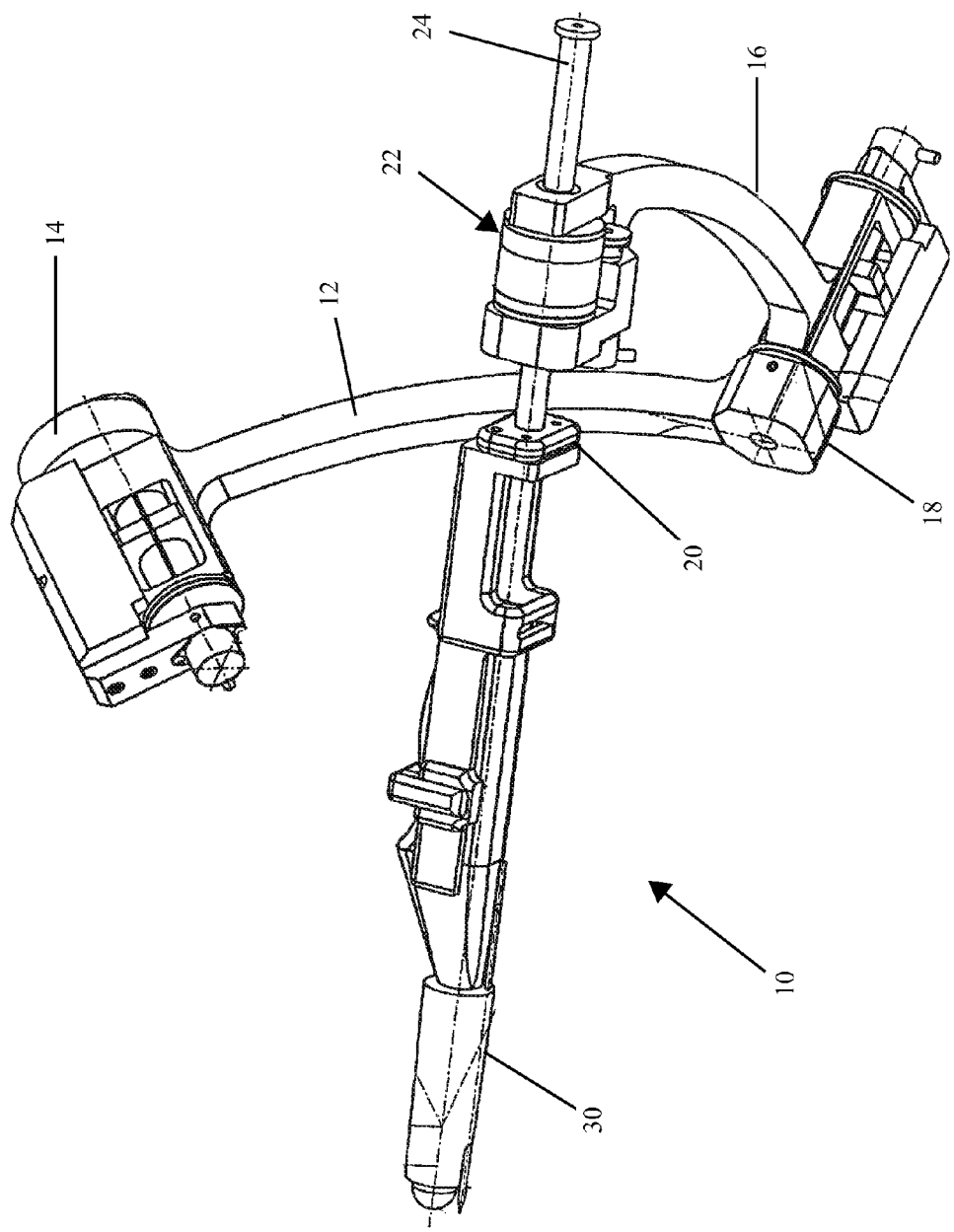
FIG. 1 illustrates one embodiment of a tracker assembly.
Figure 2:
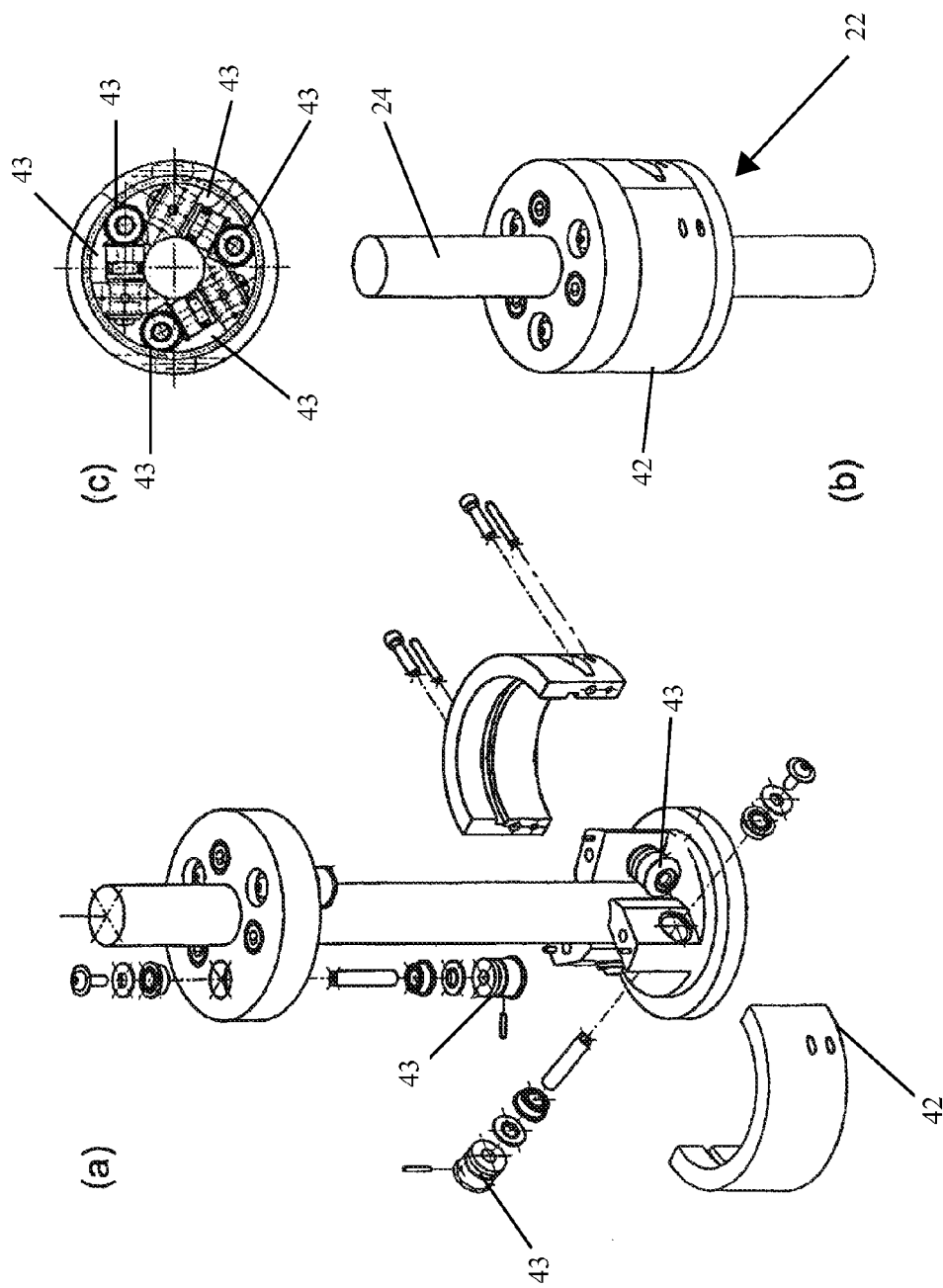
FIG. 2 illustrates a prior art rotary and linear encoder.

FIGS. 1 and 2 illustrate one prior art tracker in which aspects of the present invention may be implemented. However, it will be understood that aspects of the invention are applicable to other tracker assemblies and are considered novel by themselves. The prior art tracker is disclosed in PCT/CA2007/001076, dated Jun. 19, 2007, and is incorporated herein by reference. As shown, the tracker 10 is designed for the three-dimensional tracking of a guide for insertion of a medical tool into a body. The tracker 10 includes a first linkage 12, a second linkage 16 and a third linkage 20 that is adapted to hold a medical tool, which in this instance is represented as a trans-rectal ultrasound (TRUS) probe 30. In use, the first linkage 12 is rotatively mounted to a support (not shown) by a single degree of freedom joint 14. Likewise, the first linkage 12 and second linkage 16 are rotatively coupled by a second single degree-of-freedom joint 18. Movement of the first and second linkages 12, 16 about these joints 14, 18 allows positioning the third linkage 20 and supported probe 30 relative to a patient. The third linkage 20 interconnects to the second linkage 16 using a joint 22 that permits two degrees of freedom. Specifically, a shaft 24 of the third linkage passes through the joint 22. This shaft 24 is circular and is allowed to move through the joint 22 axially (i.e., along the axis of the shaft) as well as rotate relative to the joint 22. Tracking movement of the probe 30 requires monitoring the angular movement and the axial movement of the shaft 24.

Referring to FIG. 2, the third joint 22 of prior art tracker defines a differential assembly that performs linear motion sensing and angular motion sensing of the shaft 24. The differential assembly comprises of three pairs of miter wheels 43 that convert the longitudinal or linear motion of the main shaft along its axis to a rotational motion of the outer ring 42. The main shaft 20 has a circular cross section and thus can slide through the differential assembly and can rotate within the differential assembly simultaneously. A plastic 'O' ring of a friction wheel of a rotary encoder is coupled to the outside ring 42, and the linear motion of the main shaft is tracked by the encoder. The plastic 'O' ring of a friction wheel of another rotary encoder is coupled to the other outside ring, and the angular motion of the main shaft is sensed by the rotary encoder.

The use of the friction interfaces between the wheels of the differential assembly and the shaft as well as the outer ring can allow slippage between these components, which may affect the accuracy of position sensing. Further, the use of the differential assembly makes the prior art tracker a complicate design and costly. Additionally, the friction interface wears the 'O' rings due to the friction force based mechanism and can require frequent replacements.

Presented herein is an improved apparatus and method that permits accurate and controlled position sensing of a two-degree of freedom joint utilized with a tracker assembly that supports a medical tool. Though discussed herein as being utilized to track the position of an end-fire trans-rectal ultrasound (TRUS) probe and biopsy needle, it will be appreciated that the invention is not limited to such applications and is applicable to a wide variety of positional sensing applications for medical devices.

Figure 3:
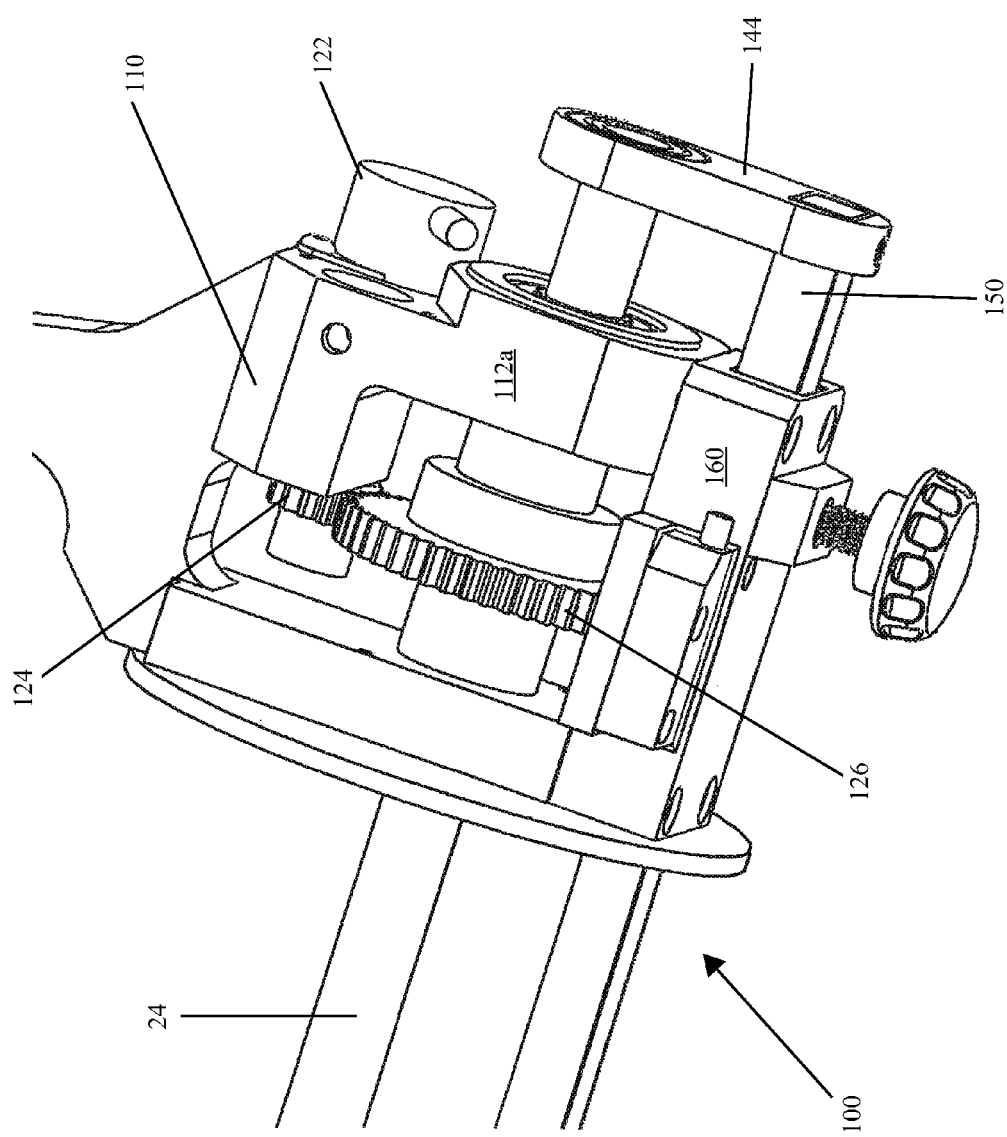
FIG. 3 illustrates a position sensor in accordance with aspects of the present invention.
Figure 4:
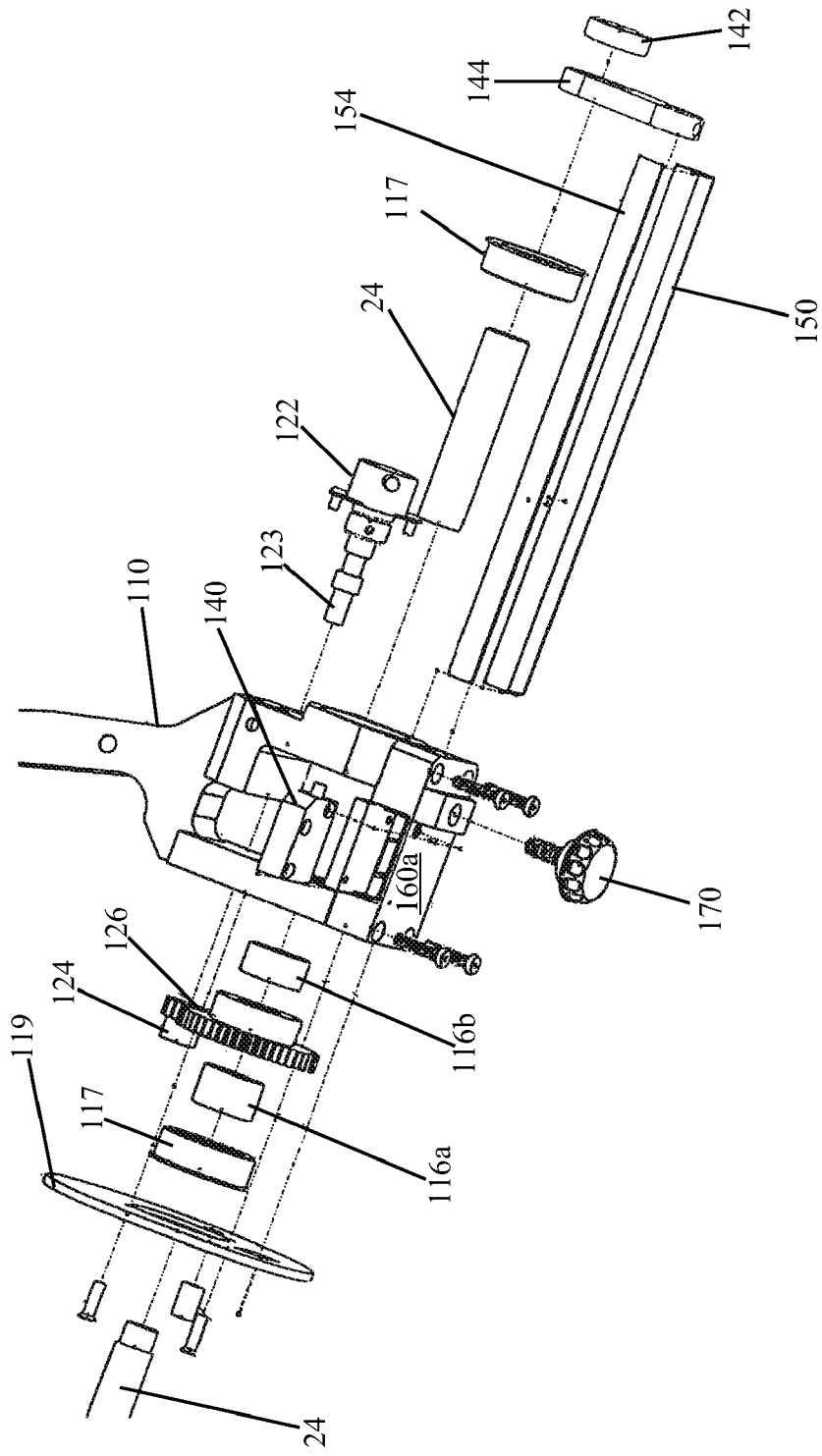
FIG. 4 illustrates an exploded view of FIG. 3.
Figure 5:
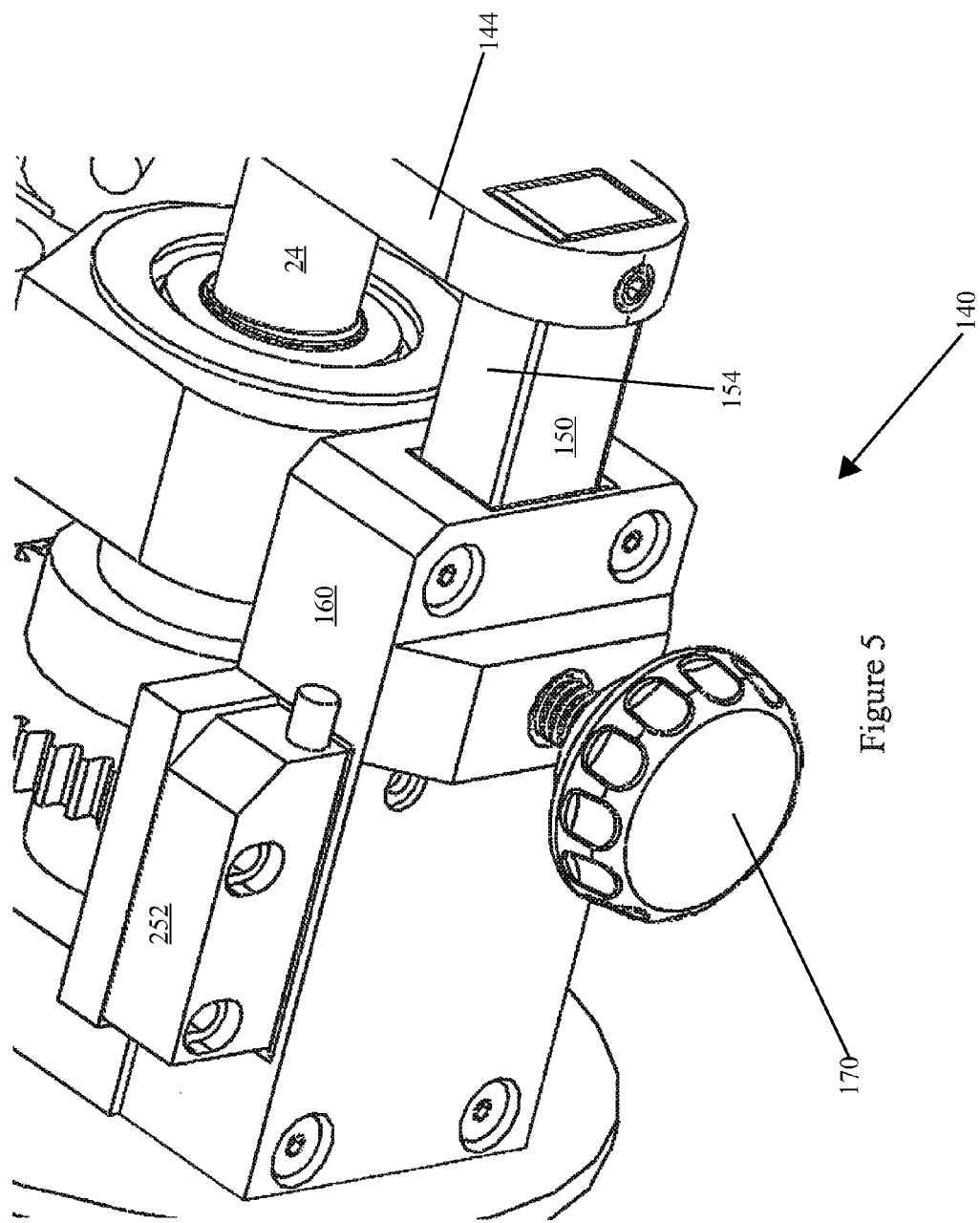
FIG. 5 illustrates the linear encoder assembly of the position sensor of FIG. 3.
Figure 6:
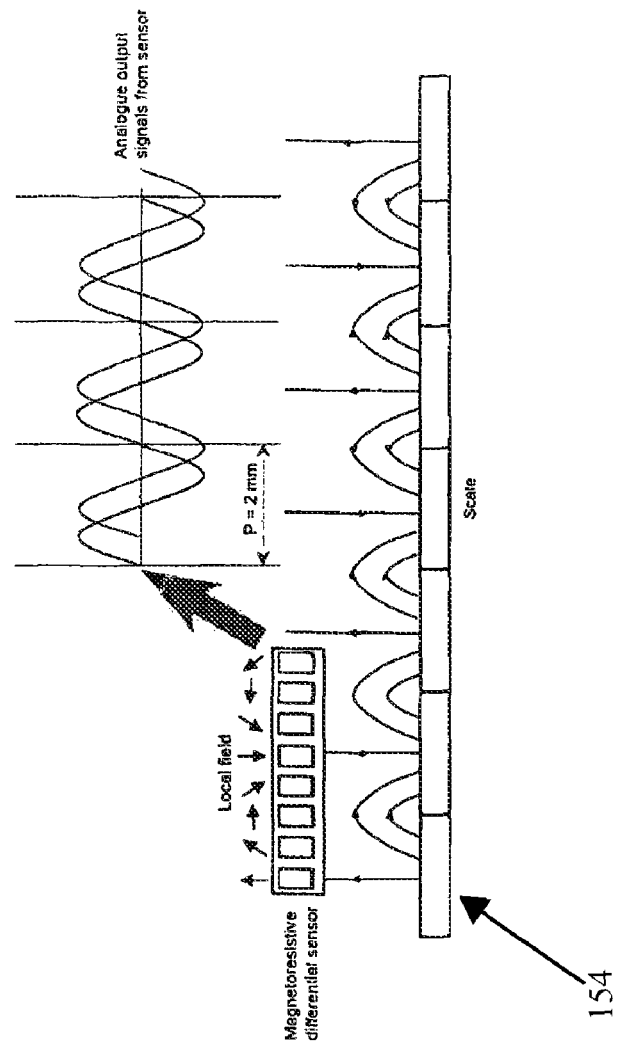
FIG. 6 illustrates a magnetic strip that may be utilized with the linear encoder of FIG. 5.
Figure 7:
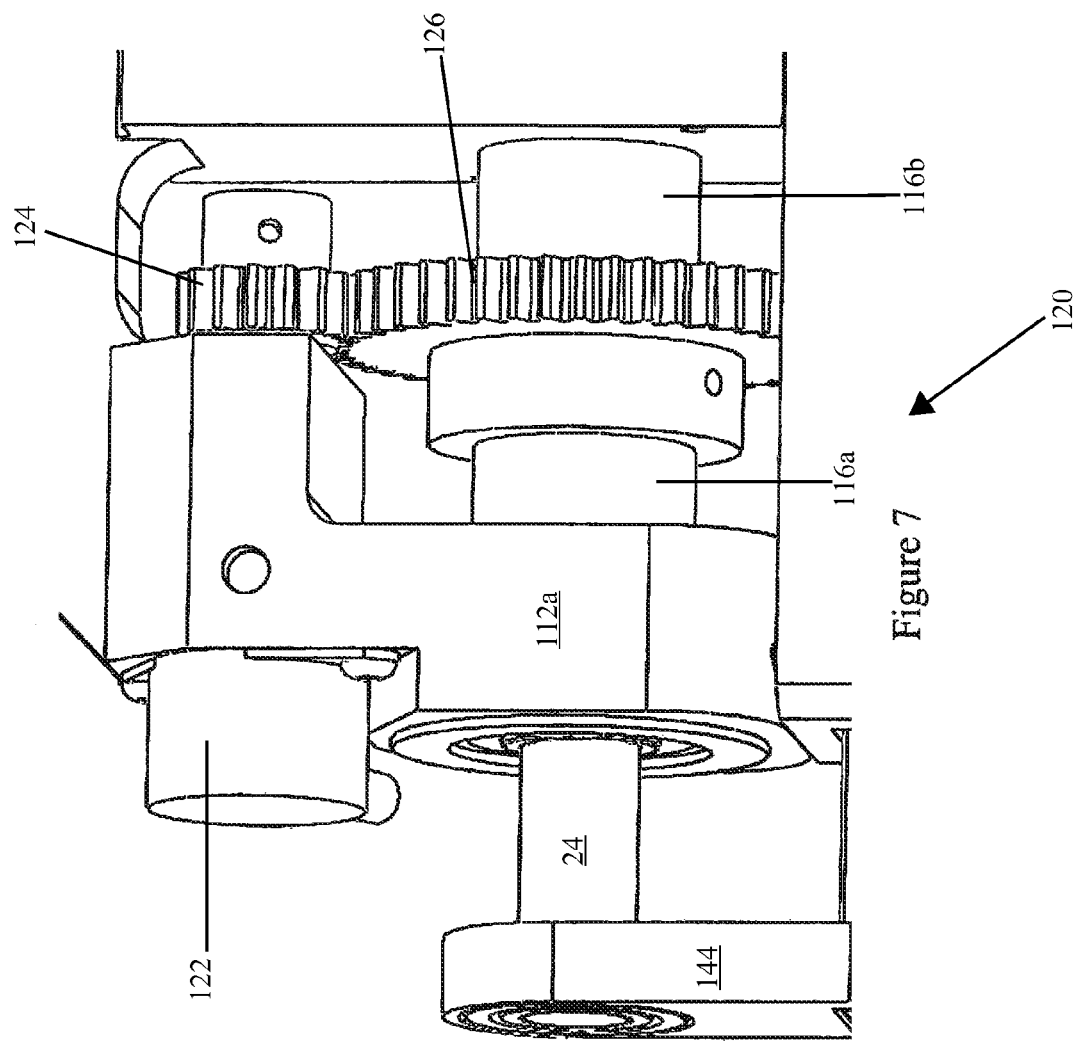
FIG. 7 illustrates the rotary encoder assembly of FIG. 3.
Figure 8:
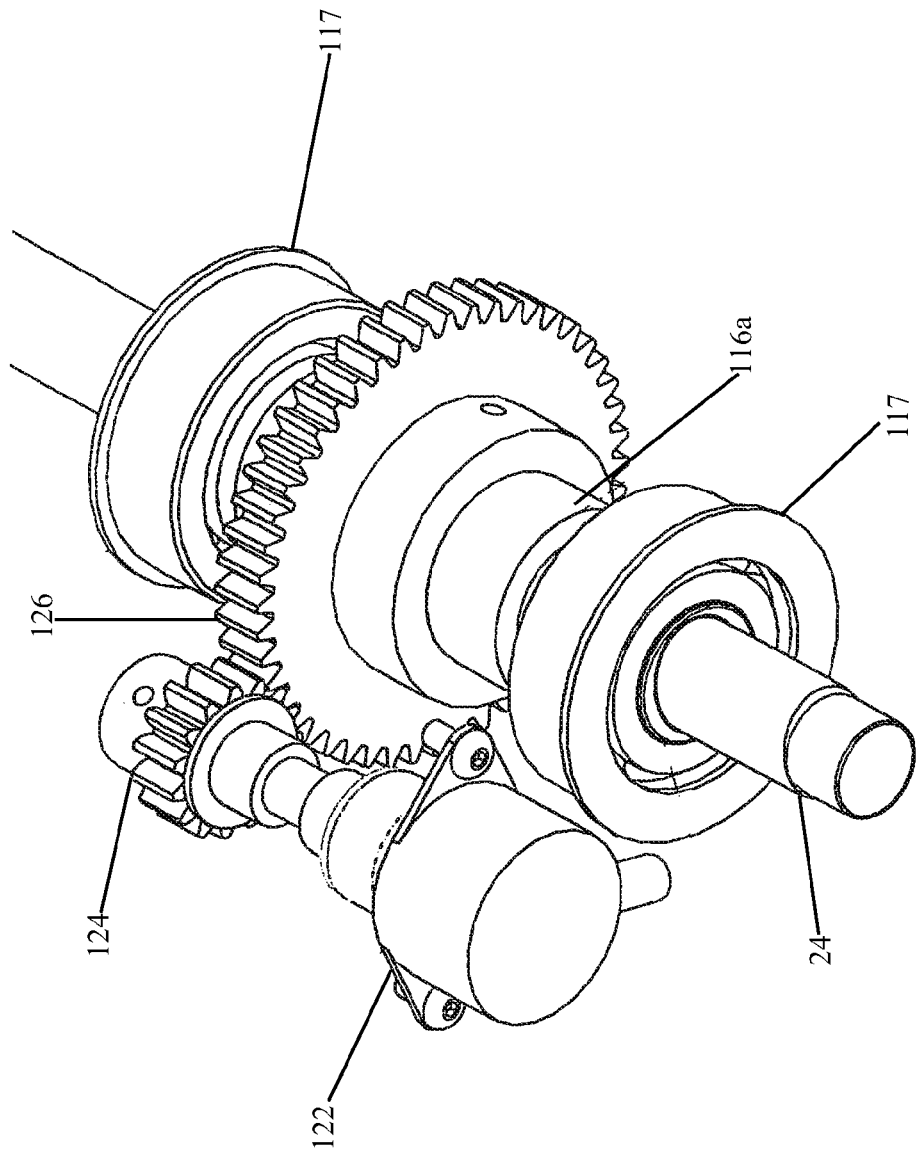
FIG. 8 illustrates the rotary encoder assembly of FIG. 3.

FIG. 3 illustrates an assembly 100 that may replace the joint 22 in the tracker of FIG. 1 or be utilized in other tracker assemblies. Importantly, the assembly 100 illustrated in FIG. 3 allows for separately monitoring the angular rotation of a shaft that supports a medical tool independently of the linear position of that shaft. In this regard, the assembly 100 includes a rotary sensor assembly 120 that is best illustrated in FIGS. 7 and 8, and a linear position sensor that is best illustrated in FIGS. 4, 5 and 6. Initially, a discussion of the rotary sensor 120 is provided after which the linear position sensor 140 is discussed.

Referring to FIGS. 3, 4, 7 and 8, the rotary sensor assembly is described. As shown, the rotary sensor assembly utilizes a rotary encoder 122 that is operative to translate rotary motion of an input shaft 123 into an electronic output that identifies the current angular position of the shaft 24 that supports a medical tool. However, the rotary encoder 122 is not directly interconnected to the shaft 24. Rather, a drive gear 126 that is mounted to the shaft 24 that engages a driven gear 124 that is mounted to the input shaft 123 of the rotary encoder 122. These gears are sometimes referred to as a revolute gear pair. When the rotary sensor assembly 120 is assembled, as illustrated in FIG. 3, the teeth of the drive gear 126 that is rotatively coupled to the shaft 24 mesh and engage with the teeth on the driven gear 124. As will be appreciated, due to meshing between these teeth, there is substantially no slip between the drive gear 126 and the driven gear 124 excepting for any lash between the gears, which may be controlled to a desired tolerance.

Figure 9A:
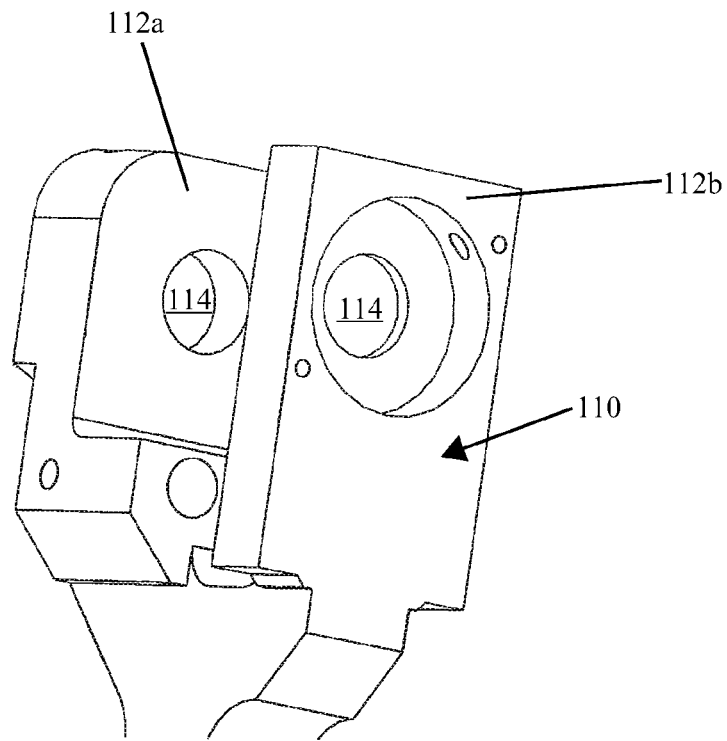
FIGS. 9A and 9B illustrate the bracket the supports the components of the position sensor assembly of FIG. 3.
Figure 9B:
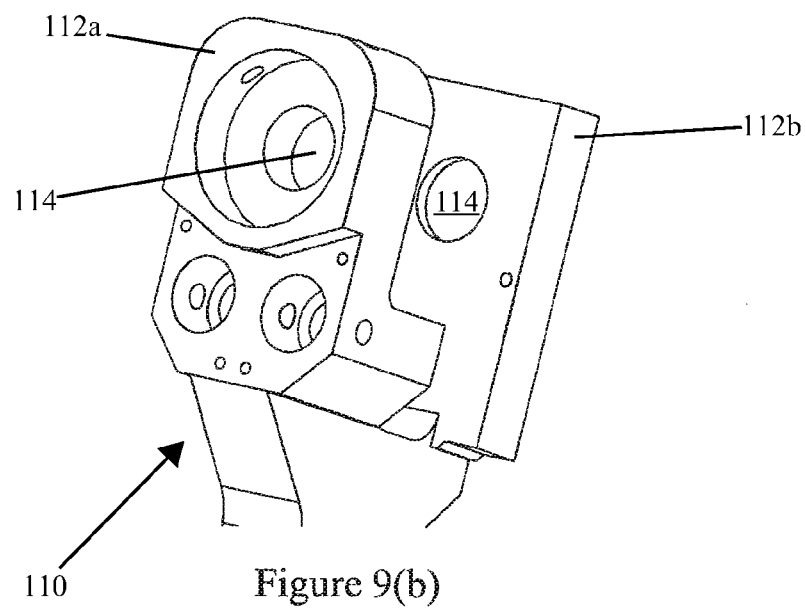

As shown in FIG. 3, the gears 124, 126 are disposed within a bracket 110 that is disposed on the end of one of the linkages of a tracker assembly. As illustrated in FIGS. 9A and 9B, the bracket 110 includes an aperture 114 that extends through first and second devises 112a, 112b. This aperture 114 is sized to receive the shaft 24 of the linkage. Furthermore, the first and second devises 112a, 112b are spaced apart to receive the drive gear and associated bearings 116a, 116b, 117 (See FIG. 4). The shaft 24 passes through the bearings and through a central aperture within the drive gear 124. However, to permit axial movement of the shaft without moving the drive gear 126, the shaft is adapted to slide through a center aperture of the drive gear 126.

However, it is necessary to translate rotational movement of the shaft 24 to the drive gear 126. That is, the shaft slides axially through the gear but rotation of the shaft rotates the gear. In the present embodiment, this is accomplished by utilizing an ovular shaft that fits within an ovular aperture through the drive gear. In this regard, it will be appreciated that the ovular shaft 24 may slide axially through the ovular aperture of the drive gear, but when rotated, the drive shaft will turn of the drive gear 126. It will be appreciated that other arrangements may be utilized. For instance, the drive shaft may be splined and fit through a splined hub within the drive gear 126. What is important is that, when the shaft 124 is rotated, such rotation is translated to the drive gear 126, which subsequently turns the driven gear 126 and is recorded by the rotary encoder 122, which generates an electronic output of such rotation.

Referring again to FIG. 3, it is noted that the rotary encoder is also mounted to the bracket 110. Accordingly, when the rotary encoder, driven gear and drive gear are mounted to the bracket, any rotary movement of the shaft 24 may be accurately recorded by the rotary encoder 122.

The bracket 110, in addition to mounting the rotary sensor assembly 120, also mounts the linear positioning sensor 240. Referring to FIGS. 3-6, the linear positioning sensor 140 is more fully described. As shown in FIG. 3, the rearward end of the shaft 24 extends through the rearward end of the clevise 112a. The shaft 24 is able to move axially along its length through the drive gear and bracket as described above. A rearward end of the shaft, however, is received within a bushing or shaft bearing 142 (See FIG. 4) that is affixed into (e.g., press fit) a fixture 144 that connects to a linear slide or link bar 150. As shown in FIG. 3, the rearward end of the link bar 150 is square such that the fixture 144 is angularly fixed relative to the link bar 150.

The link bar 150 extends through a slide bracket 160 that is interconnected to the bottom of the bracket 110. That is, the slide bracket 160 includes an aperture that is sized to permit the link bar 150 to pass therethrough. When the shaft 24 is advanced or retracted axially, this axial movement is transferred by the fixture 144 to the link bar 150, which then moves through the bracket 160. It is here that the linear position of the shaft 24 and link bar 150 is measured. In particular, the bracket 160 supports a linear magnetic encoder 152. This linear magnetic encoder is supported within the bracket 160 and is operative to read a magnetic strip 154 that is interconnected to the link bar.

The linear magnetic encoder includes a readhead that reads a magnetic position of a magnetic scale as illustrated in FIG. 6. As the magnetic scale moves relative to the readhead, the readhead detects the magnetic signature of the magnetized scale and processes these signals to generate a linear position output. Various different linear magnetic encoders are available, and one such encoder is available from RLS, a subsidiary of Renishaw PLC of Slovenia. However, it will be appreciated that other manufacturers exist and use of such linear magnetic encoders of such other manufacturers is envisioned. Such linear magnetic encoders may provide user selectable resolutions from 250 μm to 1 μm. In any case, when the shaft is moved axially along its length, the link bar and the supported strip 154 are correspondingly advanced or retracted. The linear sensor readhead typically rides at about 1.5 mm from the magnetic strip scale illustrated in FIG. 6. It will be further appreciated that the magnetic strip scale may cover the entire length of the link bar 50 such that the entire range of motion of the shaft may be monitored with an accuracy up to 1 micrometer.

As shown in FIG. 4, the magnetic strip 154 is mounted on a top surface of the link bar 150. In the present embodiment, the link bar 150 is square or rectangular, which provides a further added benefit for the present assembly 100. Particularly, the use of a square link bar provides an additional surface that may be engaged to prevent axial movement of the shaft and a supported medical tool. In the present embodiment, a threaded shaft of a locking knob 170 extends through the bracket 160 where it may engage the link bar 150. That is, a distal end of the shaft of the locking knob 170 may be engaged with a side surface of the link bar 150 in order to lock the position of the link bar, which in turn, via the fixture 144, locks the axial position of the shaft 24.

As provided, the assembly provides a robust and simple mechanism for separately measuring rotary motion of the shaft 24, as well as axial/linear motion of the shaft. Furthermore, due to the mesh engagement of the rotary gears and the magnetic contact between the linear magnetic encoder and magnetic strip, the potential slippage problem of prior art trackers is substantially reduced and/or eliminated. Furthermore, the current assembly requires lower maintenance and provides a higher reliability compared to prior art trackers that utilize friction engagements.

The invention claimed is:

1. A tracker assembly for positioning a medical tool, comprising:
    a first linkage;
    a second linkage adapted to support a medical tool proximate a free end of said second linkage, said second linkage further including a shaft;
    a joint assembly connecting said first and second linkages and providing two degrees of freedom between said linkages, said joint assembly comprising:
        a bracket interconnectable to the first linkage and having at least a first aperture for slidably and rotatively receiving the shaft of the second linkage;
        a drive gear having a central aperture for slidably receiving said shaft, wherein said drive gear is rotatively fixed relative to said shaft;
        a rotary encoder mounted to said bracket and be operatively interconnected to a driven gear, wherein teeth of the driven gear are meshed with teeth of the drive gear;
        a linear magnetic encoder mounted to said bracket, wherein said linear magnetic encoder reads a liner position of a magnetic strip that moves axially with said shaft.

2. The assembly of claim 1, further comprising:
    a bar attached to and disposed substantially in parallel with said shaft, wherein said magnetic strip is attached to said bar.

3. The assembly of claim 2, further comprising:
    a threaded knob that extends through an aperture in said bracket, wherein a distal end of said threaded knob selectively engages said bar to selectively lock the position of the bat and the shaft relative to the bracket.

4. The assembly of claim 1, wherein a portion of the shaft that extends through said drive gear has a non-circular cross-section.

* * * * *